United States Patent
Stamler et al.

(10) Patent No.: US 6,232,434 B1
(45) Date of Patent: May 15, 2001

(54) POLYMERS FOR DELIVERING NITRIC OXIDE IN VIVO

(75) Inventors: Jonathan S. Stamler, Chapel Hill; Eric J. Toone, Durham; Richard S. Stack, Chapel Hill, all of NC (US)

(73) Assignee: Duke University Medical Center, Durham, NC (US)

( * ) Notice: Subject to any disclaimer, the term of this patent is extended or adjusted under 35 U.S.C. 154(b) by 0 days.

(21) Appl. No.: 09/103,225

(22) Filed: Jun. 23, 1998

Related U.S. Application Data

(63) Continuation-in-part of application No. 08/691,862, filed on Aug. 2, 1996, now Pat. No. 5,770,645.

(51) Int. Cl.[7] .................................................. C08G 75/00
(52) U.S. Cl. ........................ 528/373; 528/422; 528/425; 536/46; 536/103; 536/122; 536/123.1; 536/126; 424/402; 424/422; 604/1
(58) Field of Search ........................ 525/54.3; 424/402, 424/422; 604/1; 528/373, 422, 425; 536/46, 163, 122, 123.1, 126

(56) References Cited

U.S. PATENT DOCUMENTS

| | | | |
|---|---|---|---|
| 4,138,535 | 2/1979 | Schweiger | 526/7 |
| 5,114,506 | 5/1992 | Consaga et al. | 149/88 |

(List continued on next page.)

FOREIGN PATENT DOCUMENTS

| | | |
|---|---|---|
| 4420523 | 6/1994 | (DE) . |
| 2 244 491 | 12/1991 | (GB) . |
| WO 93/20806 | 10/1993 | (WO) . |
| WO 94/16740 | 8/1994 | (WO) . |
| WO 94/22306 | 10/1994 | (WO) . |
| WO 95/02408 | 1/1995 | (WO) . |
| WO 95/07691 | 3/1995 | (WO) . |
| WO 95/09612 | 4/1995 | (WO) . |

(List continued on next page.)

OTHER PUBLICATIONS

Chem Abstracts: 123: 74904 "Use of Nitric Oxide Releasing Compounds As Protective Agents in is Chemia Reperfusion Injury" "Wink et al.".*

(List continued on next page.)

*Primary Examiner*—Duc Truong
(74) *Attorney, Agent, or Firm*—Hamilton, Brook, Smith & Reynolds, P.C.

(57) ABSTRACT

Disclosed are novel polymers derivatized with at least one —SNO group per 1200 atomic mass unit of the polymer. In one embodiment, the S-nitrosylated polymer has stabilized —S-nitrosyl groups. In another embodiment the S-nitrosylated polymer prepared by polymerizing a compound represented by the following structural formula:

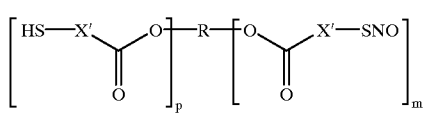

R is an organic radical.

Each X' is an independently chosen aliphatic group or substituted aliphatic group. Preferably, each X' is the same and is a C2–C6 alkylene group, more preferably —$CH_2$—, —$CH_2CH_2$—, —$CH_2CH_2CH_2$— or —$CH_2CH_2CH_2CH_2$—.

p and m are independently a positive integer such that p+m is greater than two.

The polymers of the present invention can be used to coat medical devices to deliver nitric oxide in vivo to treatment sites.

41 Claims, 2 Drawing Sheets

U.S. PATENT DOCUMENTS

| | | | |
|---|---|---|---|
| 5,116,861 | 5/1992 | Goto et al. | 514/427 |
| 5,380,758 | 1/1995 | Stamler et al. | 514/562 |
| 5,385,937 | 1/1995 | Stamler et al. | 514/557 |
| 5,385,940 | 1/1995 | Moskowitz | 514/565 |
| 5,405,919 | 4/1995 | Keefer et al. | 525/377 |
| 5,427,797 | 6/1995 | Frostell et al. | 424/434 |
| 5,482,925 | 1/1996 | Hutsell | 514/11 |
| 5,504,117 | 4/1996 | Gorfine | 514/742 |
| 5,519,020 | 5/1996 | Smith et al. | 424/718 |
| 5,525,357 | 6/1996 | Keefer et al. | 424/486 |
| 6,087,479 | 7/2000 | Stamler et al. | 530/363 |

FOREIGN PATENT DOCUMENTS

| | | |
|---|---|---|
| WO 95/09636 | 4/1995 | (WO) . |
| WO 95/10267 | 4/1995 | (WO) . |
| WO 95/12394 | 5/1995 | (WO) . |
| WO 95/13800 | 5/1995 | (WO) . |
| WO 95/13802 | 5/1995 | (WO) . |
| WO 95/24908 | 9/1995 | (WO) . |
| WO 96/02241 | 2/1996 | (WO) . |
| WO 96/02268 | 2/1996 | (WO) . |
| WO 96/15781 | 5/1996 | (WO) . |
| WO 96/15797 | 5/1996 | (WO) . |
| WO 96/16645 | 6/1996 | (WO) . |
| WO 96/17604 | 6/1996 | (WO) . |
| WO 96/28145 | 9/1996 | (WO) . |
| WO 96/35416 | 11/1996 | (WO) . |
| WO 96/38136 | 12/1996 | (WO) . |
| WO 98/05689 | 2/1998 | (WO) . |

OTHER PUBLICATIONS

123: 51297 "Use of Nitric Oxide Releasing Compounds For Hypoxic Cell Radiations Sensitizers, For Sensitizing Cells to Chemo Therapeutic Agents and For Protection of Non Cancerous Cells From Radiations or Chemotherapeutic Agents" "Mitchell et al.".*

122: 248424 Kit and Inhalation Device For Use With a Nitric Oxide Source "Eapot et al.".*

119: 109011 "S–Nitrosothiols As Smooth Muscle Relaxants and Therapeutic Uses Thereof" "Stamler et al.".*

117: 145009 Toxicity of Chemically Generated Nitric Oxide Towards Pancreatic Islet Cells Can Be Prevented By Nicotinamide "Kallrann et al.".*

89: 147197 "An Unusually Stable Thionitrite From N–Acetyl–Dif–Penicillamine; X–ray Crystal and Molecular Structure of 2(Acetylamino)–2–Carboxyl–1,1–Dimethylethyl Thionitrite" "Field et al.".*

Stamler, J. S. et al. "S–Nitrosylation of Proteins with Nitric Oxide: Synthesis and Characterization of Biologically Active Compounds," *Proc. Natl. Acad. Sci USA* 89:444–448 (Jan. 1992).

Bauer, J. A. and Ho–Leung Fung, "Chemical Stabilization of a Vasoactive S–Nitrosothiol with Cyclodextrins without Loss of Pharmacologic Activity," *Pharmaceutical Research*, 8(10):1329–1333 (1991).

Langford, E. J. et al., "Inhibition of Platelet Activity by S–Nitrosoglutathione During Coronary Angioplastry," *The Lancet*, 344:1458–1460 (1994).

Roy, B. et al., "New Thionitrites: Synthesis, Stability, and Nitric Oxide Generation," *J. Org. Chem.*, 59:7019–7026 (1994).

Gorren, A.C.F. et al., Decomposition of S–Nitrosoglutathione in the Presence of Copper Ions and Glutathione, *Arch. Biochem. Biophys. 330*(2):219–228 (1996).

Vanin, A.F. et al., "Iron Catalyzes both Decomposition and Synthesis of S–Nitrosothiols: Optical and Electron Paramagnetic Resonance Studies," Nitric Oxide: *Biology and Chemistry 1*(3) :191–203 (1997).

Barrett, J. et al., "Photochemistry of the S–Nitroso Derivatives of Hexane–1–thiol and Hexane–1,6–dithiol," *Nature 211*:848 (1966).

Bauer, J.A. and Fung, H.L., "Chemical Stabilization of a Vasoactive S–Nitrosothiol with Cyclodextrins Without Loss of Pharmacologic Activity,"*Pharmaceutical Research 8* (10):1329–1333 (1991).

Goldstein, S. and Czapski, G., "Mechanism of the Nitrosation of Thiols and Amines by Oxygenated NO Solutions: The Nature of the Nitrosating Intermediates," *J. Am. Chem. Soc. 118*:3419–3425 (1996).

Askew, S.C. et al., "Catalysis by $Cu^{2+}$ of Nitric Oxide Release From S–Nitrosothiols (RSNO)," *J. Chem. Soc. Perkin Trans. 2*:741–745 (1995).

Batsanov, A.S., et al., "Stereocontrol in Cyclisation of Dioxolanyl Radicals," *J. Chem. Soc. Perkin Trans. 1*:1281–1294 (1995).

Feelisch M. and Stamler, J.S., "Donors of Nitrogen Oxides," *Methods in Nitric Oxide Research* (M. Feelisch and J.S. Stamler, eds.), pp. 71–115, John Wiley & Sons (1996).

Arnelle, D.R. and Stamler, J.S., "$NO^+$, $NO^{\cdot}$ and $NO^-$ Donation by S–Nitrosothiols: Implications for Regulation of Physiological Functions by S–Nitrosylation and Acceleration of Disulfide Formation," *Archives of Biochemistry and Biophysics 318*(2) :279–285 (1995).

Feelisch M. and Stamler, J.S., "Preparation and Detection of S–Nitrosothiols," *Methods in Nitric Oxide Research* (M. Feelisch and J.S. Stamler, eds.), pp. 521–539, John Wiley & Sons (1996).

* cited by examiner

POLYMERS FOR DELIVERING NITRIC OXIDE IN VIVO

RELATED APPLICATIONS

This application is a continuation-in-part of U.S. Ser. No. 08/691,862, filed Aug. 2, 1996, now U.S. Pat. No. 5,770,645 the entire teachings of which are incorporated herein by reference.

BACKGROUND OF THE INVENTION

Many modern medical procedures require that synthetic medical devices remain in an individual undergoing treatment. For example, coronary and peripheral procedures involve the insertion of diagnostic catheters, guide wires, guide catheters, PTCA balloon catheters (for percutaneous transluminal coronary angioplasty) and stents in blood vessels. In-dwelling sheaths (venous and arterial), intraaortic balloon pump catheters, tubes in heart lung machines, GORE-TEX surgical prosthetic conduits and in-dwelling urethral catheters are other examples. There are, however, complications which can arise from these medical procedures. For example, the insertion of synthetic materials into lumen can cause scaring and restenosis, which can result in occlusion or blockage of the lumen. Synthetic materials in the blood vessels can also cause platelet aggregation, resulting in some instances, in potentially life-threatening thrombus formation.

Nitric oxide (referred to herein as "NO") inhibits the aggregation of platelets. NO also reduces smooth muscle proliferation, which is known to reduce restenosis. Consequently, NO can be used to prevent and/or treat the complications such as restenosis and thrombus formation when delivered to treatment sites inside an individual that have come in contact with synthetic medical devices. In addition, NO is anti-inflammatory, which would be of value for in-dwelling urethral or TPN catheters.

There are, however, many shortcomings associated with present methods of delivering NO to treatment sites. NO itself is too reactive to be used without some means of stabilizing the molecule until it reaches the treatment site. NO can be delivered to treatment sites in an individual by means of polymers and small molecules which release NO. However, these polymers and small molecules typically release NO rapidly. As a result, they have short shelf lives and rapidly lose their ability to deliver NO under physiological conditions. For example, the lifetime of S-nitroso-D,L-penicillamine and S-nitrosocysteine in physiological solution is no more than about an hour. As a result of the rapid rate of NO release by these compositions, it is difficult to deliver sufficient quantities of NO to a treatment site for extended periods of time or to control the amount of NO delivered.

Polymers containing groups capable of delivering NO, for example polymers containing diazeniumdiolate groups (NONOate groups), have been used to coat medical devices. However, decomposition products of NONOates under oxygenated conditions can include nitrosamines (Ragsdale et al., *Inorg. Chem.* 4:420 (1965), some of which may be carcinogenic. In addition, NONOates generally release NO., which is rapidly consumed by hemoglobin and can be toxic in individuals with arteriosclerosis. Further, the elasticity of known NO-delivering polymers is generally inadequate, making it difficult to coat medical devices with the polymer and deliver NO with the coated device under physiological conditions. Protein based polymers have a high solubility in blood, which results in short lifetimes. Finally, many NO-delivering polymers cannot be sterilized without loss of NO from the polymer and amounts of NO delivered are limiting.

There is, therefore, a need for new compositions capable of delivering NO to treatment sites in a manner which overcomes the aforementioned shortcomings.

SUMMARY OF THE INVENTION

The present invention is directed to novel polymers with —SNO groups, also referred to as S-nitrosyl groups. Polymers with —SNO groups are referred to as "S-nitrosylated polymers". The polymers of the present invention generally have at least one —SNO group per 1200 atomic mass units (amu) of the polymer, preferably per 600 amu of the polymer.

In one embodiment, the S-nitrosylated polymer has stabilized —S-nitrosyl groups. The polymer generally comprises at least one stabilized S-nitrosyl group per 1200 amu, and often one stabilized S-nitrosyl group per 600 amu. An S-nitrosyl group can be stabilized by a free thiol or a free alcohol from the same molecule. Each stabilized —SNO group is stabilized by a different free alcohol or thiol group. Thus, a polymer with a stabilized S-nitrosyl group generally has at least one free alcohol and/or thiol group per 1200 amu of polymer, preferably per 600 amu of polymer. Another embodiment of the present invention is an S-nitrosylated polymer prepared by polymerizing a compound represented by Structural Formula (I):

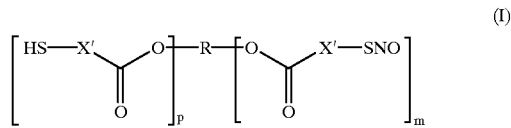

R is an organic radical.

Each X' is an independently chosen aliphatic group or substituted aliphatic group. Preferably, each X' is the same and is a C2–C6 alkylene group, more preferably —CH$_2$—, —CH$_2$CH$_2$—, —CH$_2$CH$_2$CH$_2$— or —CH$_2$CH$_2$CH$_2$CH$_2$—.

p and m are independently a positive integer such that p+m is greater than two. Preferably, p+m is less than or equal to about 8.

Another embodiment of the present invention is a method of preparing an S-nitrosylated polymer with stabilized —S-nitrosyl groups. The method comprises polymerizing a compound represented by Structural Formula (I).

In another embodiment of the present invention, the S-nitrosylated polymer is an S-nitrosylated polythiolated polysaccharide. Preferably, the polythiolated polysaccharide is a polythiolated cyclodextrin.

Another embodiment of the present invention is an S-nitrosylated polymer prepared by reacting a polythiolated polymer with a nitrosylating agent under conditions suitable for nitrosylating thiol groups. Preferably, the polythiolated polymer is a polythiolated polysaccharide.

Another embodiment of the present invention is a method of preparing an S-nitrosylated polymer. The method comprises reacting a polymer having a multiplicity of pendant thiol groups, i.e., a polythiolated polymer, with a nitrosylating agent under conditions suitable for nitrosylating free thiol groups. In a preferred embodiment, the polythiolated polymer is a polythiolated polysaccharide.

Another embodiment of the present invention is an article which is capable of releasing NO. The article is coated with at least one of the polymers of the present invention. The article can be any device for which a useful result can be achieved by NO release, including a medical device suitable for implantation at a treatment site in a subject (individual or animal). The medical device can then deliver nitric oxide to the treatment site in the subject. In another example, the article is a tube or catheter for contacting a bodily fluid of a subject.

Another embodiment of the present invention is a method of delivering nitric oxide to a treatment site in an individual or animal. The method comprises providing a medical device coated with an S-nitrosylated polymer of the present invention. The medical device is then implanted into the individual or animal at the treatment site. Nitric oxide can be delivered to a bodily fluid, for example blood, by contacting the bodily fluid with a tube or catheter coated with one or more of the polymers of the present invention.

Yet another embodiment of the present invention is a method of preparing an article capable of releasing NO, e.g., a medical device for delivering nitric oxide to a treatment site in an individual or animal or a tube or catheter for contacting a bodily fluid. The method comprises coating the article with an S-nitrosylated polymer of the present invention.

Polymers with stabilized S-nitrosyl groups and polymers obtained by polymerizing compounds represented by Structural Formula (I) can cause vasodilation in bioassays (Example 16). These polymers have also been found to deliver NO for extended periods of time lasting at least several weeks (Example 15). Thus, they are expected to be useful as coatings on medical devices for implantation in subjects, thereby delivering NO at treatment sites.

Medical devices coated with S-nitrosylated polythiolated polysaccharides are effective in reducing platelet deposition and restenosis when implanted into animal models. Specifically, stents coated with an S-nitrosylated β-cyclodextrin or an S-nitrosylated β-cyclodextrin complexed with S-nitroso-N-acetyl-D,L-penicillamine or S-nitroso-penicillamine resulted in decreased platelet deposition when inserted into the coronary or cortoid arteries of dogs compared with stents which lacked the polymer coating (Example 12). It has also been found that S-nitrosylated β-cyclodextrin and S-nitrosylated β-cyclodextrin complexed with S-nitroso-N-acetyl-D,L-penicillamine cause vasodilation in bioassays (Examples 8 and 10). Furthermore, the disclosed S-nitrosylated polysaccharides have been found to deliver NO-related activity for extended periods of time and to exhibit increased shelf stability compared with compounds presently used to deliver NO in vivo.

A further advantage of the S-nitrosylated polysaccharides is that they lack the brittleness of other NO-delivering compositions and have sufficient elasticity to coat and adhere under physiological conditions to medical devices such as stents.

DETAILED DESCRIPTION OF THE INVENTION

Figure 1:
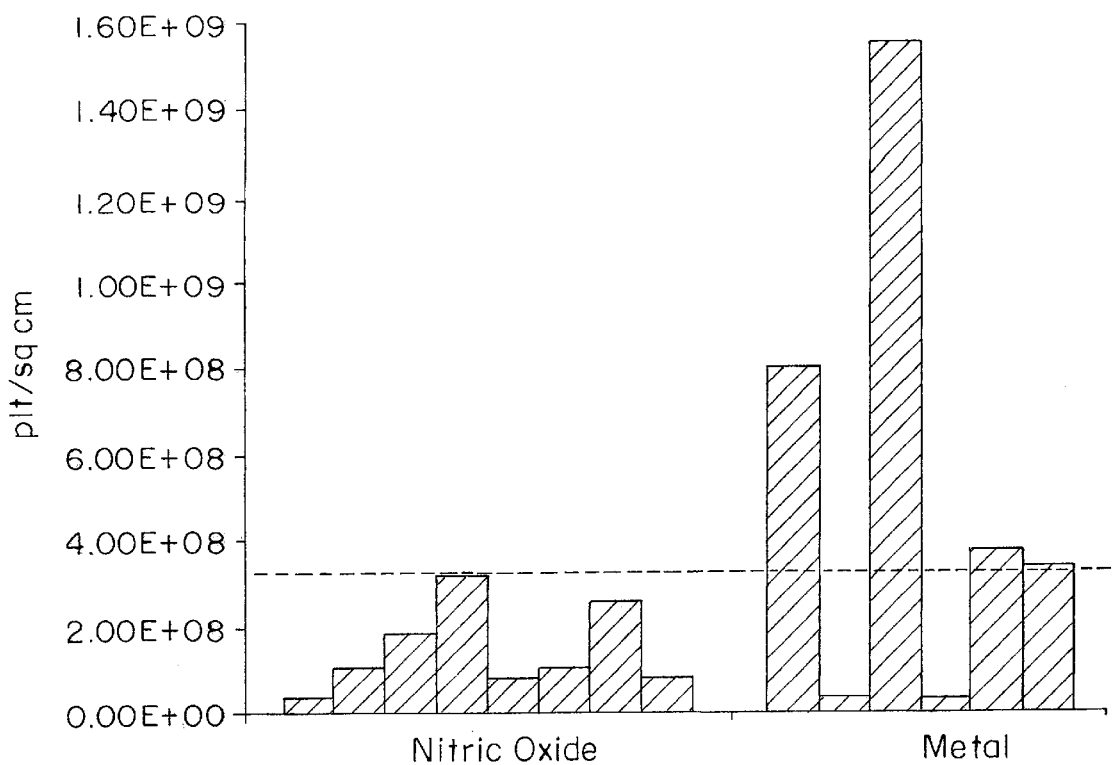
FIG. 1 is a graph illustrating the number of platelets deposited per square centimeter on stents coated with S-nitrosylated β-cyclodextrin and on uncoated control stents which had been implanted in the arteries of dogs.

As used herein "polymer" has the meaning commonly afforded the term. Examples include homopolymers (i.e., polymers obtained by polymerizing one type of monomer), co-polymers (i.e., polymers obtained by polymerizing two or more different types of monomers), including block copolymers and graft copolymers, dendritic polymers, crosslinked polymers and the like. Suitable polymers include synthetic and natural polymers (e.g. polysaccharides) as well as polymers prepared by condensation, addition and ring opening polymerizations. Also included are rubbers, fibers and plastics. Polymers can be hydrophilic, amphiphilic or hydrophobic. The polymers of the present invention are typically no n-peptide polymers.

A polymer with "stabilized S-nitrosyl groups" comprises, along with the S-nitrosyl groups, one free thiol group or free alcohol group for each stabilized S-nitrosyl group and has a half-life for NO release which is significantly greater than for the corresponding compound or polymer without free thiol or alcohol groups (e.g., about two times greater, preferably about ten times greater). Although Applicants do not wish to be bound by any particular mechanism, it is believed that an S-nitrosyl group can be stabilized by the interaction between a free thiol or a free alcohol group and the —S-nitrosyl group. A stabilizing interaction can formed, for example, when a free thiol or alcohol is located within three covalent bonds of (alpha to) an S-nitrosyl group. In another example, a stabilizing interaction can be formed when a free thiol or alcohol can be brought within about one to one and a half bond lengths of an S-nitrosyl group by energetically accessible conformational rotations of covalent bonds within the molecule.

A polymer with stabilized S-nitrosyl groups generally has a half life for NO release greater than about two hundred hours and often greater than about one thousand hours. Most known compounds which release NO have half-lives for NO release that is less than about twelve hours.

The term "organic radical", as it is used herein, refers to a moiety which comprises primarily hydrogen and carbon, but can also include small amounts of other non-metallic elements such as sulfur, nitrogen, oxygen and halogens. R, when taken together with the remainder of the molecule represented by Structural Formula (I), is a small organic molecule and typically has a molecular weight less than about 2000 amu, more typically less than 1000 amu. Thus, the compound represented by Structural Formula (I) is not a protein, polypeptide or polysaccharide.

An organic radical can also comprise functional groups which do not significantly decrease the stability of
—S-nitrosyl groups. Suitable functional groups include those which: 1) are substantially inert with respect to
—S-nitrosyl groups, i.e., groups which do not substantially increase the rate, for example, double the rate, of NO release from NO-releasing molecules; and 2) do not substantially interfere with the nitrosylation of free thiol groups, i.e. do not substantially decrease the yield (e.g., a 50% decrease in yield) of the nitrosylation or cause the formation of significant amounts of by-products. Examples of suitable functional groups include alcohols, thiols, amides, thioamides, carboxylic acids, aldehydes, ketones, halogens, double bonds, triples bonds and aryl groups (e.g, phenyl, naphthyl, furanyl, thienyl and the like).

Aliphatic groups include straight chained, branched or cyclic $C_1$–$C_8$ hydrocarbons which are completely saturated or which contain one or more units of unsaturation.

Suitable substituents for an aliphatic group are those which: 1) are substantially inert with respect to —S-nitrosyl groups, i.e., groups which do not substantially increase the rate, for example, double the rate of NO release from NO-releasing molecules; and 2) do not substantially interfere with the nitrosylation of free thiol groups, i.e. do not substantially decrease the yield of the nitrosylation (e.g., a 50% decrease in yield) or cause the formation of significant amounts of by-products. Examples of suitable substituents include halogens, C1–C5 straight or branched chain alkyl groups, alcohols, carboxylic acids, amides, thioamides, and the like.

Compounds represented by Structural Formula (I) spontaneously polymerize over a period of several days to about two weeks at room temperature to form a rubberlike NO-releasing polymer. The polymerization is generally carried out neat, but can also carried out in solution at concentrations greater than about 0.1 M, for example, in a suitable solvent such as diethyl ether. These polymers release NO for at least several weeks (Example 15). They have been shown to relax aortic smooth muscle in vitro (Example 16). Thus, they show great promise as coatings for medical devices to deliver NO to treatment sites in vivo.

The preparation of compounds represented by Structural Formula (I) is described in co-pending U.S. patent application No. 09/103,227 now U.S. Pat. No. 6,207,855 "STABLE NO-DELIVERING COMPOUNDS", filed on Jun. 23, 1998, the entire teachings of which are hereby incorporated herein by reference. Briefly, the compound is formed by nitrosylating an esterified polyol represented by Structural Formula (II):

(II)

R is an organic radical, as described above.

n is an integer greater than two, preferably an integer from three to about ten. More preferably, n is an integer from three to about eight.

Each X is independently a thiol-bearing aliphatic group or a substituted thiol bearing aliphatic group. Preferably, each X is the same thiol-bearing aliphatic group. Examples of suitable thiol-bearing aliphatic groups include —$CH_2SH$, —$CH_2CH_2SH$, —$CH_2CH_2CH_2SH$ and —$CH_2CH_2CH_2CH_2SH$. Suitable substituents for an aliphatic group are provided above.

The nitrosylation of the esterified polyol is carried out by reacting the esterified polyol with a nitrosylating agent at room temperature. Suitable nitrosylating agents are described below. Preferably about 0.5 to about 0.7 equivalents of nitrosylating agent per free thiol and free alcohol are used. S-nitroso-N-acetyl-D,L-penicillamine (SNAP) is a preferred nitrosylating agent for preparing compounds represented by Structural Formula (I). The nitrosylating agent is preferably added to the esterified polyol. The nitrosylation can be carried out neat or in solvents such as dimethyl sulfoxide, dimethyl formamide or acetonitrile at concentrations greater than about 0.01 M.

Polymers prepared by polymerizing compounds represented by Structural Formula (I) comprise monomer units represented by Structural Formula (III):

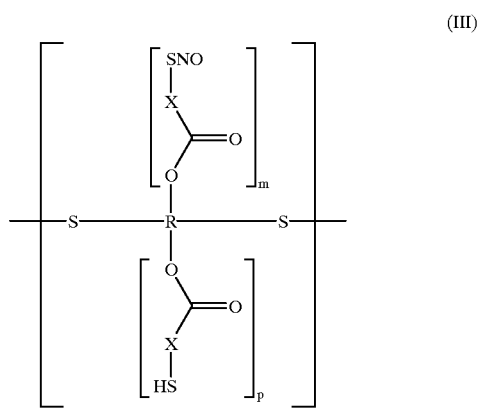

(III)

R is an organic radical, as described above.

Each X is independently a substituted or unsubstituted aliphatic group. Preferably, every X is the same. Examples of X include alkylene groups such as —$CH_2$—, —$CH_2CH_2$—, —$CH_2CH_2CH_2$— or —$CH_2CH_2CH_2CH$—.

In Structural Formula (III), p is zero or a positive interger and m is a positive integer. Preferably, p+m is less than or equal to eight.

Preferably, the monomer is represented by Structural Formula (IV):

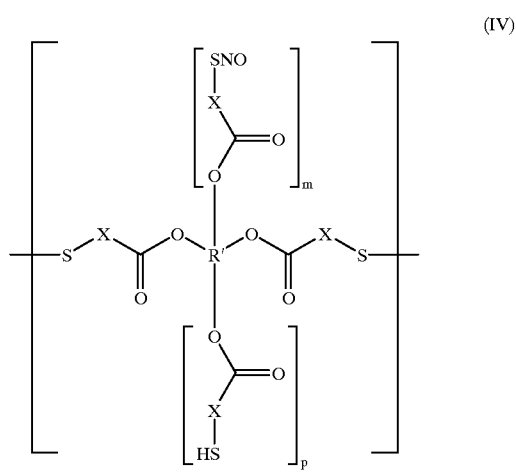

(IV)

R' is an organic radical such that —X—CO—O—R'— O—CO—X— is R. X, m and p are as described for Structural Formula (III).

S-nitrosylated polymers comprising monomers units represented by Structural Formulas (III) or (IV) can be crosslinked, as described above. For example, after an —SNO group in a monomer unit represented by Structural Formulas (III) or (IV) releases NO, the sulfur atom is available to form a disulfide bond with a thiol group in another S-nitrosylated polymer molecule. In one example, the crosslinking monomer unit is represented by Structural Formula (V):

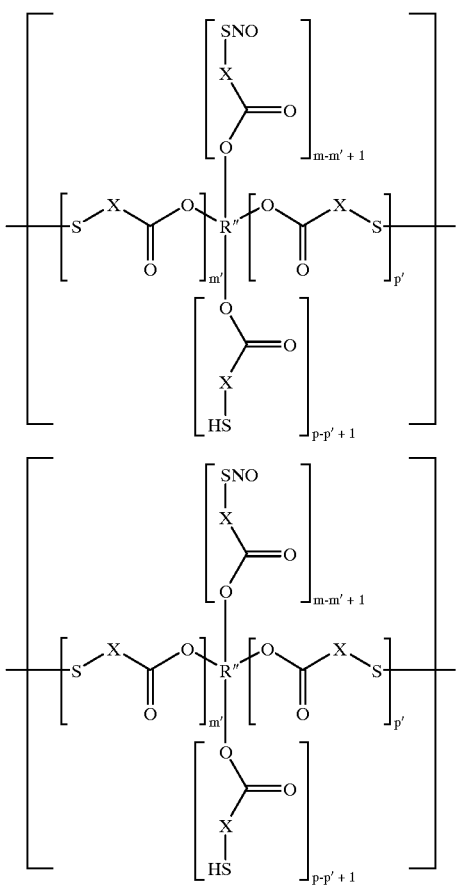

R" is an organic radical, as described above.

m' is an integer greater than 1 and less than or equal to m+1.

p' is an integer greater than or equal to one and less than or equal to p+1.

p, m and X are as described for Structural Formula (III).

S-Nitrosylated polymers can also be prepared from polymers having a multiplicity of pendant thiol groups, referred to herein as "polythiolated polymers", by reacting with a nitrosylating agent under conditions suitable for nitrosylating free thiol groups.

Suitable nitrosylating agents are disclosed in Feelisch and Stamler, "Donors of Nitrogen Oxides", *Methods in Nitric Oxide Research* edited by Feelisch and Stamler, (John Wiley & Sons) (1996), the teachings of which are hereby incorporated into this application. Suitable nitrosylating agents include acidic nitrite, nitrosyl chloride, compounds comprising an S-nitroso group S-nitroso-N-acetyl-D,L-penicillamine (SNAP), S-nitrosoglutathione (SNOG), N-acetyl-S-nitrosopenicillaminyl-S-nitrosopenicillamine, S-nitrosocysteine, S-nitrosothioglycerol, S-nitrosodithiothreitol and S-nitrosomercaptoethanol), an organic nitrite (e.g. ethyl nitrite, isobutyl nitrite, and amyl nitrite) peroxynitrites, nitrosonium salts (e.g. nitrosyl hydrogen sulfate), oxadiazoles (e.g. 4-phenyl-3-ftiroxancarbonitrile) and the like.

Nitrosylation of a polythiolated polymer with acidic nitrite can be, for example, carried out in an aqueous solution with a nitrite salt, e.g. $NaNO_2$, $KNO_2$, $LiNO_2$ and the like, in the presence of an acid, e.g. HCl, acetic acid, $H_3PO_4$ and the like, at a temperature from about $-20°$ C. to about $50°$ C., preferably at ambient temperature. Generally, from about 0.8 to about 2.0, preferably about 0.9 to about 1.1 equivalents of nitrosylating agent are used per thiol being nitrosylated. Sufficient acid is added to convert all of the nitrite salt to nitrous acid or an $NO^+$ equivalent. Specific conditions for nitrosylating a polythiolated polymer with acidic nitrite are provided in Example 3.

Nitrosylation of a polythiolated polymer with NOCl can be carried out, for example, in an aprotic polar solvent such as dimethylformamide or dimethylsulfoxide at a temperature from about $-20°$ C. to about $50°$ C., preferably at ambient temperature. NOCl is bubbled through the solution to nitrosylate the free thiol groups. Specific conditions for nitrosylating a polythiolated polymer with NOCl are provided in Example 4.

Polythiolated polymers can be formed from polymers having a multiplicity of pendant nucleophilic groups, such as alcohols or amines. The pendant nucleophilic groups can be converted to pendant thiol groups by methods known in the art and disclosed in Gaddell and Defaye, Angew. Chem. Int. Ed. Engl. 30:78 (1991) and Rojas et al., *J. Am. Chem. Soc.* 117:336 (1995), the teachings of which are hereby incorporated into this application by reference.

In one example, the S-nitrosylated polymer is an S-nitrosylated polysaccharide. Examples of suitable S-nitrosylated polysaccharides include S-nitrosylated alginic acid, κ-carrageenan, starch, cellulose, fucoidin, cyclodextrins such as α-cyclodextrin, β-cyclodextrin and γ-cyclodextrin. Other suitable examples are disclosed in *Bioactive Carbohydrates*, Kennedy and White eds., (John Wiley Sons), Chapter 8, pages 142–182, (1983) the teachings of which are incorporated herein by reference. Polysaccharides have pendant primary and secondary alcohol groups. Consequently, S-nitrosylated polysaccharides can be prepared from polythiolated polysaccharides by the methods described hereinabove. Preferred polysaccharides include cyclodextrins, for example α-cyclodextrin, β-cyclodextrin and γ-cyclodextrin. The polysaccharide is first converted to a polythiolated polysaccharide, for example, by the methods disclosed in Gaddell and Defaye and Rojas et al. In these methods primary alcohols are thiolated preferentially over secondary alcohols. Preferably, a sufficient excess of thiolating reagent is used to form perthiolated polysaccharides. Polysaccharides are "perthiolated" when all of primary alcohols have been converted to thiol groups. Specific conditions for perthiolating β-cyclodextrin are given in Examples 1 and 2. Polythiolated and perthiolated polysaccharides can be nitrosylated in the presence of a suitable nitrosylating agents such as acidic nitrite (Example 3) or nitrosyl chloride (Example 4), as described above.

In one aspect, an excess of acidic nitrite is used with respect to free thiol groups when preparing an S-nitrosylated polysaccharide, for example an S-nitrosylated cyclodextrin. An excess of acidic nitrite results in a polysaccharide with pendant —S—NO and —O—NO groups. The extent of O-nitrosylation is determined by how much of an excess of acidic nitrite is used. For example, nitrosylation of per-6-thio-β-cyclodextrin with a 50 fold excess of acidic nitrite results in a product comprising about ten moles of NO for each cyclodextrin (Example 14), or about 1 mole of NO per 140 amu. Nitrosylation of per-6-thio-β-cyclodextrin with a 100 fold excess of acidic nitrite results in a product comprising about 21 moles of NO for each cyclodextrin (Example 14), or about 1 mole of NO per 70 amu. Specific conditions for the preparation of β-cyclodextrin with pendant —O—NO and —S—NO groups are described in Example 14.

In another aspect, a polythiolated polysaceharide can be prepared by re acting the alcohol groups, preferably the primary alcohol groups, on the polysaccharide with a reagent which adds a moiety containing a free thiol or protected thiol to the alcohol. In one example the polysaccharide is reacted with a bis isocyanatoalkyldisulfide followed by reduction to functionalize the alcohol as shown in Structural Formula (VI):

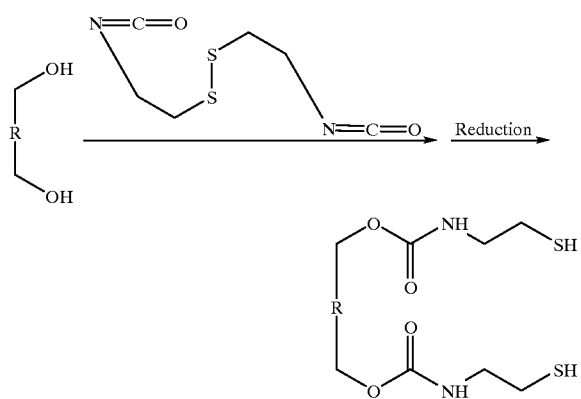

Conditions for carrying out this reaction are found in *Cellulose and its Derivatives*, Fukamota, Yamada and Tonamni, eds. (John Wiley & Sons), Chapter 40, (1985) the teachings of which are incorporated herein by reference. One example of a polythiolated polysaccharide which can be obtained by this route is shown in Structural Formula (VII):

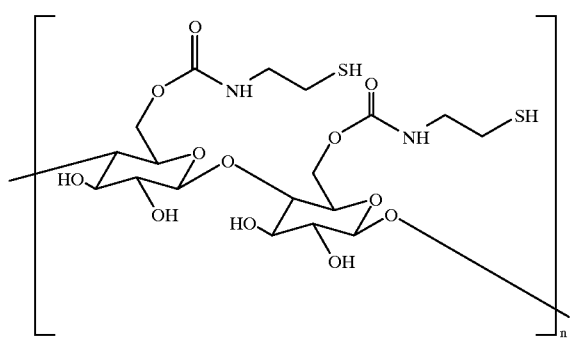

It is to be understood that agents capable of nitrosylating a free thiol, in some instances, also oxidize free thiols to form disulfide bonds. Thus, treating a polythiolated polymer (e.g. polythiolated polysaccharides such as polythiolated cyclodextrins) with a nitrosylating agent, e.g. acidified nitrite, nitrosyl chloride, S-nitrosothiols, can, in some instances, result in the formation of a crosslinked S-nitrosylated polymer matrix. A "polymer matrix" is a molecule comprising a multiplicity of individual polymers connected or "crosslinked" by intermolecular bonds. Thus, in some instances the nitrosylating agent nitrosylates some of the thiols and, in addition, crosslinks the individual polymers by causing the formation of intermolecular di sulfide bonds. Such polymer matrices are encompassed by the term "S-nitrosylated polymer" and are included within the scope of the present invention.

The quantity of —S—NO groups present in the composition can be determined by the method of Saville disclosed in "Preparation and Detection of S-Nitrosothiols," *Methods in Nitric Oxide Research*, edited by Feelisch and Stamler, (John Wiley & Sons) pages 521–541, (1996). To calculate the amount of NO per molecular weight of polymer, the polymer concentration, e.g. carbohydrate concentration, is also determined. Carbohydrate concentration can be determined by the method disclosed in Dubois et al., *Anal. Chem.* 28:350 (1956). When an excess of the nitrosylating agent is used and when the nitrosylating agent is of a sufficient size, it can be incorporated, or "entwined," within the polymeric matrix by the intermolecular disulfide bonds which crosslink the individual polymer molecules, thereby forming a complex between the polymer and the nitrosylating agent.

S-nitrosylated polysaccharides, in particular S-nitrosylated cyclized polysaccharides such as S-nitrosylated cyclodextrins, can form a complex with a suitable nitrosylating agent when more than one equivalent of nitrosylating agent with respect to free thiols in the polythiolated polysaccharide is used during the nitrosylation reaction, as described above. Generally, between about 1.1 to about 5.0 equivalents of nitrosylating agent are used to form a complex, preferably between about 1.1 to about 2.0 equivalents.

Nitrosylating agents which can complex with an S-nitrosylated cyclic polysaccharide include those with the size and hydrophobicity necessary to form an inclusion complex with the cyclic polysaccharide. An "inclusion complex" is a complex between a cyclic polysaccharide such as a cyclodextrin and a small molecule such that the small molecule is situated within the cavity of the cyclic polysaccharide. The sizes of the cavities of cyclic polysaccharides such as cyclodextrins, and methods of choosing appropriate molecules for the preparation of inclusion complexes are well known in the art and can be found, for example, in Szejtli *Cyclodextrins In Pharmaceutical,* Kluwer Academic Publishers, pages 186–307, (1988) the entire relevant teachings of which are incorporated herein by reference.

Nitrosylating agents which can complex with an S-nitrosylated cyclic polysaccharide also include nitrosylating agents with a sufficient size such that the nitrosylating agent can become incorporated into the structure of the polymer matrix of an S-nitrosylated polysaccharide. As discussed earlier, in certain instances nitrosylation of polythiolated polymers can also result in the crosslinking of individual polymer molecules by the formation of intermolecular disulfide bonds to give a polymer matrix. Suitable nitrosylating agents are those of an appropriated size such that the nitrosylating agent can be incorporated into this matrix. It is to be understood that the size requirements are determined by the structure of each individual polythiolated polymer, and that suitable nitrosylating agents can be routinely determined by the skilled artisan according to the particular S-nitrosylated polymer being prepared.

Nitrosylating agents which can form a complex with S-nitrosylated cyclodextrins include compounds with an S-nitroso group (S-nitroso-N-acetyl-D,L-penicillamine (SNAP), S-nitrosoglutathione (SNOG), N-acetyl-S-nitrosopenicillaminyl-S-nitrosopenicillamine, S-nitrosocysteine, S-nitrosothioglycerol, S-nitrosodithiothreitol, and S-nitrosomercaptoethanol), an organic nitrite (e.g. ethyl nitrite, isobutyl nitrite, and amyl nitrite), oxadiazoles (e.g. 4-phenyl-3-furoxancarbonitrile), peroxynitrites, nitrosonium salts and nitroprusside and other metal nitrosyl complexes (See Feelisch and Stamler, "Donors of Nitrogen Oxides," *Methods in Nitric Oxide Research* edited by Feelisch and Stamler, (John Wiley & Sons) (1996). As discussed in greater detail below, NO delivery times and delivery capacity of S-nitrosylated cyclodextrins are increased by the incorporation of nitrosylating agents. The extent and degree to which delivery times and capacity are increased is dependent on the nitrosylating agent.

Specific conditions for forming a complex between an S-nitrosylated cyclodextrin and a nitrosylating agent are provided in Examples 5 and 6. Conditions described in these examples result in nitrosylation of at least some of the free thiols in the polysaccharide. Because an excess of nitrosylating agent is used with respect to the quantity of free thiols in the polysaccharide is used, the resulting composition contains unreacted nitrosylating agent. Evidence that the S-nitrosylated polysaccharide forms a complex with the nitrosylating agent comes from the discovery, reported herein, that the ate of NO release from the reaction product of per-(6-deoxy-6—thio)β-thiocyclodextrin and S-nitroso-N-acetylpenicillamine is extended compared with S-nitroso-N-acetylpenicillamine alone (Example 10).

Although Applicants do not wish to be bound by any particular mechanism, it is believed that incorporation of a nitrosylating agent into the S-nitrosylated cyclic polysaccharide allows both the polysaccharide and the nitrosylating agent to deliver NO at a treatment site. It is also believed that the interaction between the cyclic polysaccharide and the nitrosylating agent results in stabilization of the —S—NO functional group in the nitrosylating agent. It is further believed that the presence of a nitrosylating agent in the composition serves to feed, i.e. replenish, the nitrosyl groups in the S-nitrosylated polysaccharide, thereby serving to extend the lifetime during which the polymer can serve as an NO donor. The degree to which the lifetime of an S-nitrosylated cyclic polysaccharide can be extended is determined by the stability of the S-nitrosyl group when the nitrosylating agent is a thionitrite. The stability of —S—NO groups is dependent on a number of factors; the ability of —S—NO groups to chelate metals facilitates homolytic breakdown; tertiary —S—NO groups are more stable than secondary —S—NO groups which are more stable than primary groups; —S—NO groups which fit into the hydrophobic pocket of cyclodextrins are more stable than those which do not; the proximity of amines to the —S—NO group decreases stability; and modification at the position , to the —S—NO group regulates stability.

In one embodiment, the present invention is a composition comprising a polymer of the present invention and at least one other ingredient which endow the polymer with desirable characteristics. For example, plasticizers and elastomers can be added to the composition to provide the polymer with greater elasticity. Generally, suitable plasticizers and elastomers are compounds which are: 1) biocompatible, i.e. which cause minimal adverse reactions such as platelet and protein deposition in an individual to which it is administered and 2) which are soluble in the polymer capable of delivering NO and which can, in turn, solubilize said polymer. Examples of suitable plasticizers include polyalkylene glycols such as polyethylene glycols. Preferred plasticizers are those which can also deliver NO, for example nitrosothioglycerol.

Another embodiment of the present invention is a method of delivering NO to a treatment site in a subject (individual or animal) using the novel polymers and compositions of the present inventions to deliver NO. A "treatment site" includes a site in the body of an individual or animal in which a desirable therapeutic effect can be achieved by contacting the site with NO. An "individual" refers to a human. Suitable animals include veterinary animals such as dogs, cats and the like and farm animals such as horses, cows, pigs and the like.

Treatment sites are found, for example, at sites within the body which develop restenosis, injury or thrombosis as a result of trauma caused by contacting the site with a synthetic material or a medical device. For example, restenosis can develop in blood vessels which have undergone coronary procedures or peripheral procedures with PTCA balloon catheters (e.g. percutaneous transluminal angioplasty). Restenosis is the development of scar tissue from about three to six months after the procedure and results in narrowing of the blood vessel. NO reduces restenosis by inhibiting platelet deposition and smooth muscle proliferation. NO also inhibits thrombosis by inhibiting platelets and can limit injury by serving as an anti-inflammatory agent.

A treatment site often develops at vascular sites which are in contact with a synthetic material or a medical device. For example, stents are often inserted into blood vessels to prevent restenosis and re-narrowing of a blood vessel after a procedure such as angioplasty. Platelet aggregation resulting in thrombus formation is a complication which may result from the insertion of stents. NO is an antiplatelet agent and can consequently be used to lessen the risk of thrombus formation associated with the use of these medical devices. Other examples of medical devices which contact vascular sites and thereby increase the risk of thrombus formation include sheaths for veins and arteries and GORE-TEX surgical prosthetic.

Treatment sites can also develop at non-vascular sites, for example at sites where useful therapeutic effect can be achieved by reducing an inflammatory response. Examples include the airway, the gastrointestinal tract, bladder, uterine and corpus cavernosum. Thus, the compositions, methods and devices of the present invention can be used to treat respiratory disorders, gastrointestinal disorders, urological dysfumction, impotence, uterine dysfunction and premature labor. NO delivery at a treatment site can also result in smooth muscle relaxation to facilitate insertion of a medical device, for example in procedures such as bronchoscopy, endoscopy, laparoscopy and cystoscopy. Delivery of NO can also be used to prevent cerebral vasospasms post hemorrhage and to treat bladder irritability, urethral strictures and biliary spasms.

Treatment sites can also develop external to the body in medical devices used to treat bodily fluids temporarily removed from body for treatment, for example blood. Examples include conduit tubes within heart lung machines, tubes of a dialysis apparatus and catheters.

The method of delivering NO to a treatment site in an individual or animal comprises implanting a medical device coated with a polymer of the present invention at the treatment site. NO can be delivered to bodily fluids, for example blood, by contacting the bodily fluid with a medical device coated with a polymer of the present invention. Examples of treatment sites in an individual or animal, medical devices suitable for implementation at the treatment sites and medical devices suitable for contacting bodily fluids such as blood are described in the paragraphs hereinabove.

"Implanting a medical device at a treatment site" refers to bringing the medical device into actual physical contact with the treatment site or, in the alternative, bringing the medical device into close enough proximity to the treatment site so that NO released from the medical device comes into physical contact with the treatment site. A bodily fluid is contacted with a medical device coated with a polymer of the present invention when, for example, the bodily fluid is temporarily removed from the body for treatment by the medical device, and the polymer coating is an interface between the bodily fluid and the medical device. Examples include the removal of blood for dialysis or by heart lung machines.

In one embodiment of the present invention, an article, for example a medical device, tube or catheter, is coated with a polymer of the present invention. In one example, the article is coated with an S-nitrosylated polysaccharide, preferably a cyclic S-nitrosylated polysaccharide, and even more preferably an S-nitrosylated cyclodextrin. A mixture is formed by combining a solution comprising a polythiolated polysaccharide with an article insoluble in the solution. The mixture is then combined with a nitrosylating agent under conditions suitable for nitrosylating free thiol groups, resulting in formation of an S-nitrosylated polysaccharide. In an aqueous solution, the S-nitrosylated polysaccharide precipitates from the solution and coats the article. In polar aprotic solvents such as dimethylformamide (DMF) or dimethylsulfoxide (DMSO), the article can be dipped into the reaction mixture and then dried in vacuo or under a stream of an inert gas such as nitrogen or argon, thereby coating the article. Suitable nitrosylating agents include acidified nitrite, S-nitrosothiols, organic nitrite, nitrosyl chloride, oxadiazoles, nitroprusside and other metal nitrosyl complexes, peroxynitrites, nitrosonium salts (e.g. nitrosyl hydrogensulfate) and the like.

In another example, the article is coated with a polymer having stabilized S-nitrosyl groups or a polymer obtained by polymerizing a compound represented by Structural Formula (I). The polymer is dissolved in a suitable solvent. The article is then dipped into the solution and then dried in vacuo or under a stream of an inert gas such as nitrogen or argon, thereby coating the article. Alternatively, the article is coated with a compound represented by Structural Formula (I) which is then allowed to polymerize.

The polymers of the present invention are not brittle, and consequently remain adhered to the article, even under physiological conditions. Thus, these polymers are particularly suited for coating medical devices which are to be implanted in patients for extended periods of time.

It is to be understood that other methods of applying polymer coatings to articles, including methods known in the art, can be used to coat articles with the polymers of the present invention.

Another embodiment of the present invention is a method of replacing a loss of NO groups from an S-nitrosylated polymer. As discussed above, NO is lost from S-nitrosylated compounds over time. In addition, sterilization of medical instruments containing S-nitrosylated compounds also results in the loss of NO from S-nitrosylated compounds. The loss of NO from S-nitrosylated compounds reduces the capacity of the compound to deliver NO to a treatment site. NO groups can be replaced by contacting the S-nitrosylated polymer with an effective amount of a gaseous, nitrosylating agent such as nitrosyl chloride or nitric oxide.

The invention is further illustrated by the following examples, which are not intended to be limiting in any way.

EXEMPLIFICATION

Example 1

Preparation of Per-(6-deoxy-6-iodo)-γ-iodocyclodextrin

β-Cyclodextrin (20.0 g, 17.6 mmol, 123 mmol primary hydroxyl) was added to a stirred solution of triphenylphosphine (97.2 g, 371 mmol, 3 eq per primary hydroxyl) and iodine chips (93.5 g, 371 mmol, 3 eq per primary hydroxyl) in dimethylformamide (DMF) (400 mL); the mixture warmed on addition. The solution was placed in an oil bath at 80° C. for 20 hours, then permitted to cool to room temperature DMF (350 mL) was removed under reduced pressure to yield a thick, the dark syrup was roughly one-third the volume of the original solution. To this syrup, cooled in an ice bath, was added 160 mL of 3 M NaOMe; the pH was found to be 9 (pH paper with a drop of water). After addition, the syrup was permitted to warm to room temperature and stirred for an additional 1 hour. The syrup was then poured into MeOH (3600 mL) to give a small amount of precipitate. Water (1000 mL) was added slowly to the MeOH solution, yielding a milky white precipitate in the dark brown solution. The precipitate was removed by filtration to give a yellow solid that was washed several times with MeOH (1000 mL total) to remove most of the color, giving a tan solid that was Soxhlett-extracted for >12 hours and dried under high vacuum to give 19.84 of an off-white solid (59%).

Example 2

Preparation of Per-(6-deoxy-6—thio)β-thiocyclodextrin

Per-(6-deoxy-6-iodo)-β-cyclodextrin (19.84 g, 10.4 mmol, 72.9 mmol primary iodide) was dissolved in DMF (210 mL) and thiourea (6.3 g, 82.8 mmol, 1.13 eq) was added. The solution was stirred at 70° C. under nitrogen for 48 hours. DMF was removed under reduced pressure to give an orange oil, which was added to aqueous NaOH (5.4 g in 1000 mL, 135 mmol) to give a white precipitate on stirring. The solution was heated to a gentle reflux for 1 hour, which effected full solvation of the precipitate, then cooled, which resulted in formation of a precipitate that was removed by filtration and washed with water (this precipitate was not used). The solution was acidified with 1 M $KHSO_4$ to give a fine white precipitate that was filtered and washed with water, then air-dried overnight. The precipitate was suspended in water (700 mL), then solvated by addition of 70 mL of aqueous 1 M NaOH, then re-precipitated with 90 mL of aqueous 1 M $KHSO_4$. The precipitate was filtered, air-dried overnight, then dried under high vacuum to give 6.0 g (46%) of an off-white solid, mp 289° C. (dec).

Example 3

Nitrosylation of Per-6-thio-β-cyclodextrin with Acidic Nitrite

Per-(6-deoxy-6-thio)-β-cyclodextrin (500 mg, 0.401 mmol, 2.81 mmol primary thiol) was dissolved in 0.5 M aqueous NaOH (10 mL) to give a faintly yellow solution. A mixture of 2.8 mL 1 M aqueous $NaNO_2$ (2.8 mmol, 1 equivalent per mole free thiol) and 2 M HCl (15 mL) was quickly added to give a brick-red precipitate. The precipitate was pelleted by centrifuge, and the acidic supernatant was removed by syringe. Deionized water was added and the precipitate was agitated to full dispersion. The centrifugation/supernatant removal process was repeated six times (until the supernatant was neutral to pH paper), giving a deep red pellet in a small amount of water.

Example 4

Nitrosylation of per-6-thio-β-cyclodextrin with Nitrosyl Chloride in DMF

Per-(6-deoxy-6-thio)-β-cyclodextrin (50 mg, 0.04 mmol, 0.28 mmol primary thiol) was dissolved in DMF (1 mL).

Nitrosyl chloride was bubbled through to give a deep brown solution. The solvent can be removed in vacuo or under a stream of an inert gas such as nitrogen or argon to afford the polymer product.

Example 5

Nitrosylation of Per-6-thio-β-cyclodextrin with S-Nitroso-N-Acetylpenicillamine

Per-(6-deoxy-6-thio)-β-cyclodextrin (32.3 mg, 0.0259 mmol, 0.181 mmol primary thiol) was dissolved in 1 mL 1 M NaOH. D(+)-S-nitroso-N-acetylpenicillamine (57.0 mg, 1.4 eq per thiol) was added to give a deep-red precipitate. The precipitate was pelleted by centrifuge, and the acidic supernatant was removed by syringe. Deionized water was added and the precipitate was agitated to full dispersion. The centrifugation/supernatant removal process was repeated four times (until the supernatant was neutral to pH paper), giving a deep red pellet in a small amount of water.

Example 6

Nitrosylation of Per-6-thio-β-cyclodextrin with S-Nitroso-N-Acetylpenicillamine in Dimethylformamide Per-(6-deoxy-6-thio)-β-cyclodextrin (10 mg, 0.0080 mmol, 0.056 mmol primary thiol) was dissolved in 1 mL DMF. D(+)-S-nitroso-N-acetylpenicillamine (17.7 mg, 0.080 mmol, 1.4 eq per thiol) was added to give a green solution. After standing for 2 hours, the solution had turned deep red. The solvent can be removed in vacuo or under a stream of an inert gas such as nitrogen or argon to afford the polymer product.

Example 7

Method for Assaying Nitric Oxide Release

The capacity of a compound to cause relaxation of vascular smooth muscle, measured by the degree and duration of vasodilation resulting from exposure of a blood vessel to the compound, is a measure of its ability to deliver NO in vivo. Methods reported in Stamler et al., *Proc. Natl. Acad. Sci. USA* 89:444 (1992), Osborne et a., *J. Clin. Invest.* 83:465 (1989) and the chapter by Furchgott in *Methods in Nitric Oxide Research*, edited by Feelisch and Stamler, (John Wiley & Sons) (1996), were used to measure vascular smooth muscle contraction. Because lower concentrations of NO are required to inhibit platelet aggregation than vasodilation, measurement of smooth muscle contraction provides a good indication of whether a composition delivers sufficient NO to reduce platelet aggregation. New Zealand White female rabbits weighing 3–4 kg were anesthetized with sodium pentobarbital (30 mg/kg). Descending thoracic aorta were isolated, the vessels were cleaned of adherent tissue, and the endothelium was removed by gentle rubbing with a cotton-tipped applicator inserted into the lumen. The vessels were cut into 5-mm rings and mounted on stirrups in 20 mL organ baths. The rings were suspended under a resting force of 1 g in 7 ml of oxygenated Kreb's buffer (pH 7.5) at 37° C. and allowed to equilibrate for one hour. Isometric contractions were measured on a Model 7 oscillograph recorder connected to transducers (model TO3C, Grass Instruments, Quincy, Mass.). Fresh Krebs solution was added to the bath periodically during the equilibration period and after each test response. Sustained contractions were induced with 7 µM norepinephrine prior to the addition of the test compound.

Example 8

Delivery of Nitric Oxide by a Polymer Coated Stent

The ability of S-nitrosylated β-cyclodextrin (referred to as "free polymer") to cause continuous vasodilation was compared with the NO-related activity of a stent coated with S-nitrosylated β-cyclodextrin. S-nitrosylated β-cyclodextrin was obtained by the method described in Example 3. Polymer-coated stents were obtained by suspending a stent in the reaction mixture prepared according to the procedure described in Example 3, thereby allowing the precipitated S-nitrosylated β-cyclodextrin to coat the stent. Alternatively, polymer-coated stents were obtained by dipping a stent into a reaction mixture prepared by the method of Example 4. In either case, the polymer-coated stent was then dried in vacuo or under a stream of a nitrogen. The delivery of NO by the polymer coated stent and by the free polymer was assayed according to the procedure described in Example 7.

The polymer coated stent resulted in continuous vasodilation for more than one hour. Removal of the stent resulted in immediate restoration of tone, indicative of continuous NO release.

A fresh polymer coated stent was added to the organ chamber. The stent was then removed from the organ chamber and transferred to a second organ chamber. Similar levels of smooth muscle relaxation were observed to occur in each organ chamber, which is indicative of continuous release of NO from the S-nitrosylated β-cyclodextrin.

Example 9

Stability of Polymers Prepared by Nitrosylating Per-6-Thio-β-Cyclodextrin with S-Nitroso-N-Acetylpenicillamine The S-nitrosylated polymer prepared by the method described in Example 5 was placed on a metal base and dried in vacuo or under a stream of nitrogen to give a brown solid. This solid had an absorabance of about 15 in the visible range from about 540 to about 600 nanometers. Concentrations of NO in the 1.0 mM range are sufficient to give an absorbance of about 0.15 in this region of the visible spectrum.

The polymer was then stored and protected from light for three weeks. The absorbance in the region from about 540–600 nanometers was essentially unchanged, indicating retention of S—NO by the polymer. In addition, the ability of the compound to cause vasodilation, as measured by the assay described in Example 7, also remained essentially unchanged over the three week period.

Example 10

Incorporating S-Nitroso-N-Acetylpenicillamine Into S-Nitrosylated Polymers Increases the Nitric Oxide Delivering Capacity and Half-Life of the Polymers S-Nitroso-penicillamine, S-nitrosylated β-cyclodextrin (prepared according to the procedure in Example 3) and S-nitrosylated β-cyclodextrin complexed with S-nitroso-penicillamine (prepared according to the procedure in Example 5) were assayed by the method described in Example 7 for their ability to cause vasodilation. In addition, the half-lives for these compositions in physiological solution were measured. The half-life is time required for the composition to lose one half of its bound NO. The amount of NO in the composition is determined by the method of Saville, as described in Example 13.

S-nitrosylated β-cyclodextrin complexed with S-nitroso-penicillamine was found to deliver several orders of magnitude more NO in physiological solution than S-nitroso-penicillamine. In addition, S-nitroso-penicillamine was able to deliver NO for no more than about one hour, while S-nitrosylated β-cyclodextrin complexed with S-nitroso-penicillamine had a half-life of greater than forty hours. This result indicates that incorporating S-nitroso-penicillamine into the polymer matrix results in stabilization of the S-nitroso-penicillamine —S—NO group.

Incorporation of S-nitroso-penicillamine into the polymer matrix of S-nitrosylated β-cyclodextrin resulted in an extension of the time period during which nitric oxide can released. The half-life of S-nitrosylated β-cyclodextrin was greater than about eighteen hours, while the half-life of S-nitrosylated β-cyclodextrin complexed with S-nitroso-penicillamine was greater than about forty hours. This result indicates that it is possible to extend the time period during which S-nitrosylated polymers can release NO, based on the type of NO donor that is incorporated into the polymer matrix. This result also suggests that the NO donor is "empowering" the polymer with NO activity, thus serving to extend the polymer lifetime.

Example 11

Assay For Determining Antiplatelet Effects

Venous blood, anticoagulated with 3.4 mM sodium citrate was obtained from volunteers who had not consumed acetylsalicylic acid or any other platelet-active agent for at least 10 days. Platelet-rich plasma was prepared by centrifugation at 150 xg for 10 minutes at 25° C. Platelet counts were determined with a Coulter Counter (model ZM).

Aggregation of platelet-rich plasma was monitored by a standard nephelometric technique, in which 0.3-ml aliquots of platelets were incubated at 37° C. and stirred at 1000 rpm in a PAP-4 aggregometer (Biodata, Hatsboro, Pa.).

S-Nitrosylated β-cyclodextrin, prepared according to the method described in Example 3, was incubated at concentrations of 1 $\mu$M, 10 $\mu$M and 100 $\mu$M in 400 $\mu$L of platelet rich plasma for 3 minutes. Aggregations were induced by adding 100 $\mu$L of 10 $\mu$M ADP. Controls were run in the absence of polymer. Aggregations were quantified by measuring the maximal rate and extent of change of light transmittance and are expressed as normalized value relative to control aggregations.

Dose-dependent inhibition of ADP-induced platelet aggregation was observed over the range of 1 $\mu$M to 100 $\mu$M S-nitrosylated β-cyclodextrin. Inhibition of platelet aggregation was observed, even at the lowest concentration.

Example 12

Inhibition of Platelet Deposition in Dogs by S-Nitrosylated β-Cyclodextrin Coated Stent Platelets play a central role in the development of acute closure as well as late restenosis following angioplasty. Potent inhibitors of the platelet glycoprotein $II_B/III_A$ when given systemically have been shown to be effective in reducing 30 day and 6 month clinical events following high risk angioplasty. This benefit, however, has come at the expense of higher rates of bleeding complications. By delivery of a potent glycoprotein $II_B/III_A$ inhibitor locally, the benefits of platelet inhibition may be attained without the risk of systemic platelet inhibition. The purpose of this study is to determine the local platelet inhibitory effects of cyclodextrin-nitric oxide.

Methods

Seven mongrel dogs were studied. After diagnostic angiography, stents were implanted into the LAD and LCX arteries. The first 3 animals received plain 8 mm corrugated metal ring stents and the remaining 4 were given SNO-cyclodextrin coated stents. Coronary dimensions were obtained utilizing on-line QCA measurements and stents were appropriately sized to achieve a 1.2–13:1 stent to artery ratio. Prior to stent implantation, autologous platelets were labeled with Indium 111 oxime, reinfused and allowed to recirculate for 1 hour. The assigned stents were then deployed at 10–14 ATMs and quantitative coronary angiography was repeated. Platelets were allowed to circulate an additional 24 hours then the study was terminated for platelet deposition analysis.

Results

Platelet deposition on plain metal stents was greater than on NO coated stents although the difference was not statistically significant: 5.19±5.78 vs. 4.03±5.33 platelets×$10^8$/$cm^2$ p=0.5827. However, 4 of the 6 metal controls had greater platelet deposition than any of the NO coated stents. The mean for the metal controls was affected by 2 very low values. These data suggest that the drug prevents above baseline platelet deposition as was seen in 4 of the 6 metal stents without NO coating. The number of platelets/square centimeter on each of the control stents and on each of the coated stents are shown in FIG. 1.

Example 13

Determination of the Amount of S-Nitrosylation in S-Nitrosylated Polysaccharides Determination of Carbohydrate Concentration The amount of carbohydrate present is determined by the following disclosed in Dubois et al., *Anal. Chem.* 28:350 (1956). Two milliliters of carbohydrate solution containing between 10 and 70γ of carbohydrate are pipetted into a colorimetric tube, and 0.05 ml of 80% phenol is added. Then 5 ml of concentrated sulfuric acid is added rapidly, the stream of acid being directed against the liquid surface rather than against the side of the test tube in order to obtain good mixing. The tubes are allowed to stand 10 minutes, then they are shaken and placed for 10 to 20 minutes in a water bath at 25° C. to 30° C. before readings are taken. The color is stable for several hours and readings may be made later if necessary. The absorbance of the characteristic yellow-orange color is measured at 490 m$\mu$ of hexoses and 480 m$\mu$ for pentose and uronic acids. Blanks are prepared by substituting distilled water for sugar solution. The amount of sugar may then be determined by reference to a standard curve previously constructed for the particular sugar under examination.

All solutions are prepared in triplicate to minimize errors resulting from accidential contamination with cellulose lint.

Determination of R—S—NO Concentration

The concentration of R—S—NO groups in a sample is based on the method reported in Saville, *Analyst* 83:620 (1958). By this method, R—S—NO groups are converted into an azo dye. The concentration of this dye is determined by measuring the absorbance at 540 nm ($\epsilon$~50,000 $M^{-1}$ $cm^{-1}$). The procedure is as follows:

Reagents

Solution A: sulfanilamide 1% dissolved in 0.5 M HCl.
Solution B: same solution as used in A to which 0.2% $HgCl_2$
Solution C: 0.02% solution of N-(1-naphthyl)-ethylenediamine dihydrochloride dissolved in 0.5 M HCl.

Procedure

A given volume (50 $\mu$l-1m) of the sample to be assayed is added to an equivalent volume of solution A and solution B.

The two samples are set aside for 5 minutes to allow formation of the diazonium salt, after which an equivalent volume of solution C is added to each mixture. Color formation, indicative of the azo dye product, is usually complete by 5 minutes. The sample absorbance is then read spectrophotometrically at 540 nm. The RSNO is quantified as the difference in absorbance between solution B and A. (i.e. B−A). In the event that the background nitrite concentration is high (i.e. increased background in A), the accuracy of the measurement can be increased by the addition of an equivalent volume of 0.5% ammonium sulfamate in acid (45 mM) 5 minutes prior to the addition of sulfanilamide. The nitrous acid in solution reacts immediately with excess ammonium sulfamate to form nitrogen gas and sulfate.

Concentrations of thiol greater than 500 $\mu$M in samples may interfere with the assay if nitrite is also present at micromolar concentration. Because nitrite will nitrosate indiscriminantly under the acidic conditions employed, thiols will effectively compete for reaction with sulfanilamide (present at 50 mM in this assay) as their concentration approaches the millimolar range. This will lead to artifactual detection of RSNO. The problem can be avoided by (1) keeping the ratio of thiol to sulfanilamide <0.01, (2) first alkylating thiols in the solution, or (3) adding free thiols to standards to correct for the potential artifact.

Figure 2:
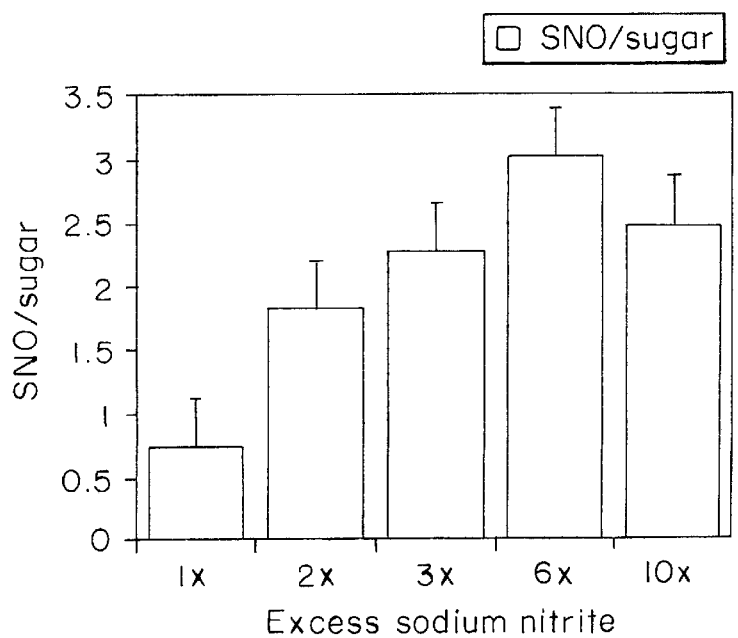
FIG. 2 is a graph illustrating the number of —S—NO groups per cyclodextrin on the product resulting from the reaction of per-6-thio-β-cyclodextrin with one (1×), two (2×), three (3×), six (6×) and ten (10×) equivalents of acidic nitrite.

S-nitrosylated β-cyclodextrin was prepared as described in Example 3 using 1 mM perthiolated β-cyclodextrin and 1) one equivalent (1×); 2) two equivalents (2×); three equivalents (3×); six equivalents (6×); and ten equivalents (10×) of acidic nitrite. The carbohydrate concentration and the —S—NO concentration of each resulting carbohydrate polymer was then determined, as described above. The results are shown in FIG. 2. A six fold excess of acidified nitrite results in about three —S—NO groups per molecule of cyclodextrin, or about one —S—NO group per 470 molecular weight. The use of three and ten equivalents of acidified nitrite results in a product with between about 2 and 2.5 —S—NO groups per cyclodextrin.

Example 14

Preparation of O- and S-Nitrosylated β-Cyclodextrin

β-Cyclodextrin with pendant —O—NO and —S—NO groups was prepared according to the procedure described in Example 3 except that 50 and 100 equivalents of acidic nitrite were used.

The formation of —O—NO groups is accompanied by an increase in absorbance in the 320–360 nm range of the ultraviolet/visible spectrum. Because —S—NO groups also absorb in this region of the ultraviolet/visible spectrum, confirmation of O-nitrosylation is provided by the observation that the increase in absorbance in the 320–360 nm region is accompanied by no further increase in the —S—NO concentration. The concentration of —S—NO is determined by the method of Saville, described in Example 13. The amount of —O—NO present in the polymer can be determined by the intensity of the absorbance in the 320–360 nm region and the loss of NO from media. The quantity of —O—NO per molecular weight can be calculated by first determining the carbohydrate concentration, as described in Example 13 above.

Figure 3:
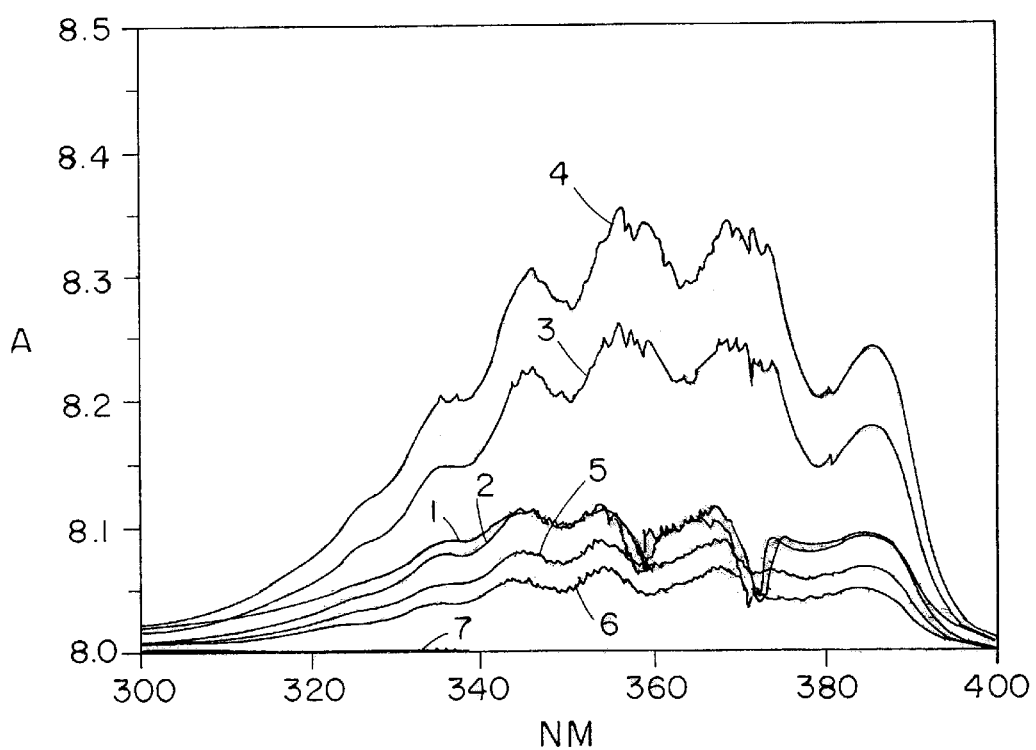
FIG. 3 is the visible/ultraviolet spectrum of a reaction mixture comprising β-cyclodextrin and a 50 fold excess of acidic nitrite, taken at intervals of (1) 5 minutes, (2) fifteen minutes, (3) thirty minutes, (4) forty-five minutes, (5) sixty minutes, (6) seventy five minutes and (7) ninety minutes.

FIG. 3 shows the ultraviolet/visible spectrum of the β-cyclodextrin in the presence of a 50 fold excess of acidic nitrite, as described above. As can be seen, the absorbance in the 340–350 nm region increases over time, with a maximum being reached after about 45 minutes. The combined concentration of —O—NO and —S—NO groups was determined to be about 10 NO groups per cyclodextrin when a 50 fold excess of acidic nitrite were used or about one NO group per 140 amu. The combined concentration of —O—NO and —S—NO groups was determined to be about 21 NO groups per cyclodextrin when a 100 fold excess of acidified nitrite were used or about one NO group per 67 amu.

Example 15

General Procedure for the Preparation of Polymers With Stabilized S-Nitrosylated Groups All precursor thiols were obtained from Sigma-Aldrich Chemical Co. and were used without further purification. Tertiary-butyl nitrite (TBN, 96%) was purchased from Aldrich Chemical Co. and was used without further purification.

Polythiol and TBN were mixed neat and allowed to stir at room temperature. 0.5 equivalents of TBN were used for each equivalent of free thiol present in the polythiol. The reaction vessel was then sealed to exclude oxygen and wrapped in aluminum foil to exclude light.

The following polythiols were reacted with TBN according to the procedure described in the previous paragraph:

Polythiol 1 - Trimethylolpropane Tris(3-Mercaptopropionate)

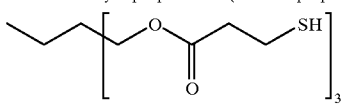

Polythiol 2 - Pentaerythritol Tetrakis-(3-Mercaptopropionate)

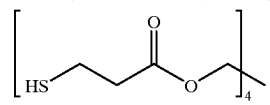

Polythiol 3 - 1,2,6-Hexanetriol Trithioglycolate

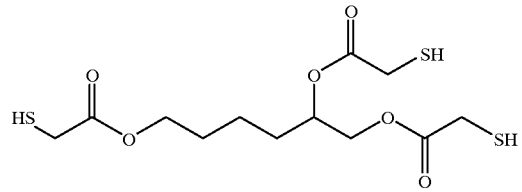

Polythiol 4 - Trimethylolpropane Tris(2-Mercaptoacetate)

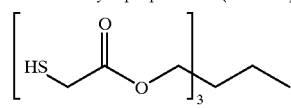

In each case, the reaction mixture rapidly turned a deep red after mixing the polythiol and TBN. The red color is indicative of S-nitrosylation. After standing for about two weeks, each reaction mixture appeared as a pink-gel like solid. The color persisted in each case for at least three weeks, indicating that the polymers retained the ability to release NO was retained during this period of time. As shown in Example 16, polymers that were one week old released sufficient NO to relax vascular smooth muscle.

Example 16

Relaxation of Vascular Smooth Muscle by the Polymers With Stabilized S-nitrosyl Groups The capacity of the polymers prepared in Example 15 to relax vascular smooth muscle was determined by the method described in Example 7, modified to use descending thoracic aorta obtained from Wistar rats. 20.5 mg of Polythiol 1, 7.1 mg of Polythiol 2, 25.5 mg of Polythiol 3 and 6.6 mg of Polythiol 4 were tested independently. All polymers had been prepared at least one week prior to testing. In each case, relaxation of the smooth muscle occurred within one minute of adding the test polymer.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A polymer comprising at least one —SNO group per 600 amu of the polymer and at least one free alcohol or free thiol group per 600 amu of the polymer, wherein:

a) at least one —SNO group per 600 atomic mass unit is stabilized by one of the free thiol or free alcohol groups; and b) each stabilized —SNO group is stabilized by a different free alcohol or free thiol group.

2. The polymer of claim 1 wherein the polymer comprises monomer units represented by the following structural formula:

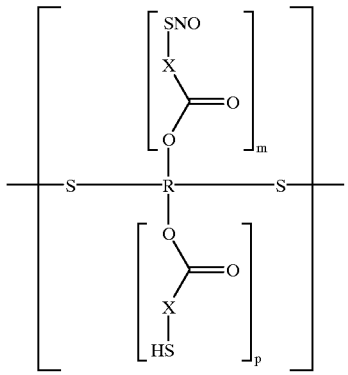

wherein:

R is an organic radical;

each X is independently a substituted or unsubstituted aliphatic group;

p is zero or a positive integer; and m is a positive integer.

3. The polymer of claim 2 wherein the polymer comprises monomer units represented by the following structural formula:

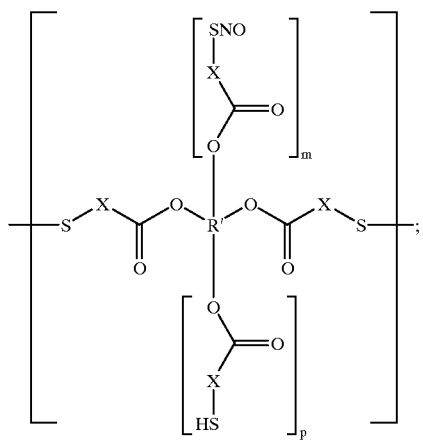

wherein R' is an organic radical such that —X—CO—O—R'—O—CO—X— is R.

4. The polymer of claim 3 wherein every X is the same.

5. The polymer of claim 4 wherein p+m is less than or equal to about eight.

6. The polymer of claim 5 wherein each X is —$CH_2$—, —$CH_2CH_2$—, —$CH_2CH_2CH_2$— or —$CH_2CH_2CH_2CH$—.

7. The polymer of claim 6 wherein the polymer is crosslinked.

8. The polymer of claim 7 wherein the crosslinking monomer is represented by the following structural formula:

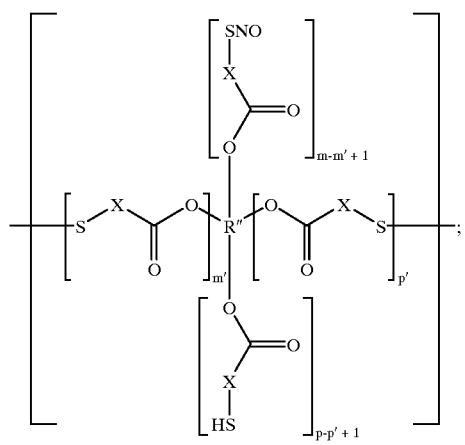

wherein:

R" is an organic radical;

m' is an integer greater than 1 and less than or equal to m+1; and p' is an integer greater than or equal to one and less than or equal to p+1.

9. A polymer comprising one or more —SNO groups, wherein at least one of the —SNO groups is stabilized by a free thiol group or a free alcohol group.

10. A polymer prepared by polymerizing a compound represented by the following structural formula:

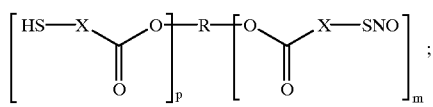

wherein:

R is an organic radical;

each X is independently a substituted or unsubstituted aliphatic group; and p and m are each a positive integer such that p+m is greater than two.

11. The polymer of claim 10 wherein every X is the same.

12. The polymer of claim 11 wherein p+m is less than or equal to about eight.

13. The polymer of claim 12 wherein each X is —CH$_2$—, —CH$_2$CH$_2$—, —CH$_2$CH$_2$CH$_2$— or —CH$_2$CH$_2$CH$_2$CH—.

14. A method of preparing a polymer comprising stabilized S-nitrosyl groups, said method comprising the step of polymerizing a compound represented by the following structural formula:

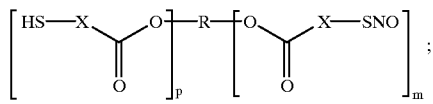

wherein:

R is an organic radical;

each X is independently a substituted or unsubstituted aliphatic group; and p and m are each a positive integer such that p+m is greater than two.

15. The method of claim 14 wherein every X is the same.

16. The method of claim 15 wherein p+m is less than or equal to about eight.

17. The polymer of claim 16 wherein each X is —CH$_2$—, —CH$_2$CH$_2$—, —CH$_2$CH$_2$CH$_2$— or —CH$_2$CH$_2$CH$_2$CH—.

18. An article capable of releasing NO wherein the article is coated with a polymer comprising at least one —SNO group per 600 amu of the polymer and at least one free alcohol or free thiol group per 600 amu of the polymer, wherein:

a) at least one —SNO group per 600 atomic mass unit is stabilized by one of the free thiol or free alcohol groups; and ii) each stabilized —SNO group is stabilized by a different free alcohol or free thiol group.

19. The article of claim 18 wherein the article is a medical device for implantation in a subject or a tube or catheter for contacting a bodily fluid of a subject.

20. The article of claim 19 wherein the polymer comprises monomer units represented by the following structural formula:

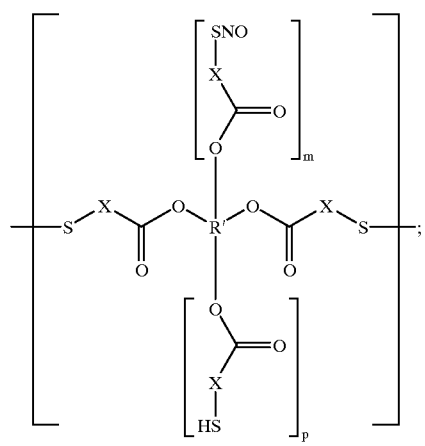

wherein:

R' is an organic radical;

each X is independently a substituted or unsubstituted aliphatic group;

p is zero or a positive integer; and m is a positive integer.

21. The article of claim 19 wherein the article is coated with a polymer obtained by polymerizing a compound represented by the following structural formula:

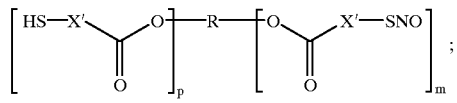

R is an organic radical;

each X' is an independently chosen aliphatic group or substituted aliphatic group; and p and m are independently a positive integer such that p+m is greater than two.

22. The article of claim 19 wherein the polymer is an S-nitrosylated polysaccharide.

23. The article of claim 22 wherein the S-nitrosylated polysaccharide is an S-nitrosylated polythiolated cyclodextrin.

24. The article of claim 19 wherein the article is coated with a polymer obtained by nitrosylating a polythiolated polysaccharide.

25. The article of claim 24 whrein the polythiolated polysaccharide is a polythiolated cyclodextrin.

26. A method of delivering nitric oxide to a treatment site in a subject or to bodily fluid comprising the steps of:

a) providing a medical device coated with a polymer comprising at least one —SNO group per 600amu of the polymer and at least one free alcohol or free thiol group per 600 amu of the polymer, wherein:

i) at least one —SNO group per 600 atomic mass unit is stabilized by one of the free thiol or free alcohol groups; and ii) each stabilized —SNO group is stabilized by a different free alcohol or free thiol group; and b) implanting the medical device at the treatment site or contacting the bodily fluid with the medical device.

27. The method of claim 26 wherein the polymer comprises monomer units represented by the following structural formula:

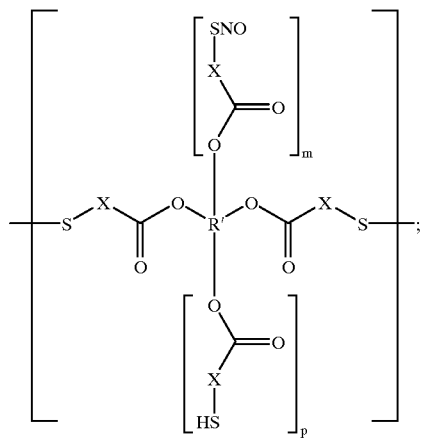

wherein:

R is an organic radical;

each X is independently a substituted or unsubstituted aliphatic group;

p is zero or a positive integer; and m is a positive integer.

28. The method of claim 26 wherein the polymer is obtained by polymerizing a compound represented by the following structural formula:

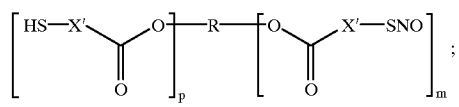

R is an organic radical;

each X' is an independently chosen aliphatic group or substituted aliphatic group; and p and m are independently a positive integer such that p+m is greater than two.

29. The method of claim 26 wherein the polymer is an S-nitrosylated polysaccharide.

30. The method of claim 29 wherein the S-nitrosylated polysaccharide is an S-nitrosylated polythiolated cyclodextrin.

31. The method of claim 26 wherein the polymer is prepared by nitrosylating a polythiolated polysaccharide.

32. The method of claim 31 wherein the polythiolated polysaccharide is a polythiolated cyclodextrin.

33. A method of preparing an article capable of releasing NO, said method comprising coating an article with a polymer comprising at least one —SNO per 600 amu of the polymer and at least one free alcohol or free thiol group per 600 amu of the polymer, wherein:

a) at least one —SNO grouper 600 atomic mass unit is stabilized by one of the free thiol or free alcohol groups; and b) each stabilized —SNO group is stabilized by a different free alcohol or free thiol group.

34. The method of claim 33 wherein the article is a medical device for delivering nitric oxide to a treatment site in a subject or a tube or catheter for contacting a bodily fluid of a subject.

35. The method of claim 34 wherein the polymer comprises monomer units represented by the following structural formula:

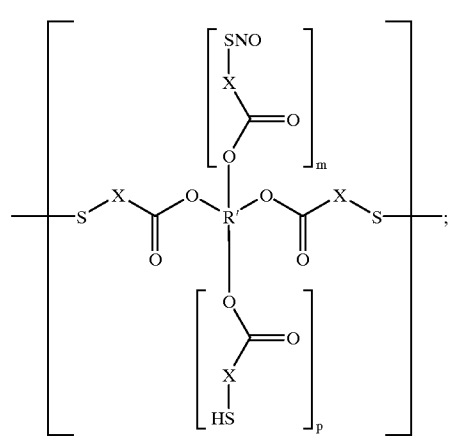

wherein:

R' is an organic radical;

each X is independently a substituted or unsubstituted aliphatic group;

p is zero or a positive integer; and m is a positive integer.

36. The method of claim 34 wherein the polymer is obtained by polymerizing a compound represented by the following structural formula:

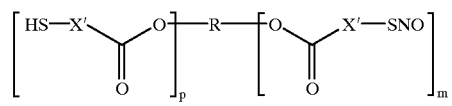

wherein:

R is an organic radical;

each X' is an independently chosen aliphatic group or substituted aliphatic group; and p and m are independently a positive integer such that p+m is greater than two.

37. The method of claim 34 wherein the polymer is an S-nitrosylated polysaccharide.

38. The method of claim 37 wherein the S-nitrosylated polysaccharide is an S-nitrosylated polythiolated cyclodextrin.

39. The method of claim 37 wherein the polymer is obtained by nitrosylating a polythiolated polysaccharide.

40. The method of claim 39 wherein the polythiolated polysaccharide is a polythiolated cyclodextrin.

41. A polymer prepared by reacting a solution comprising a cyclic polythiolated polysaccharide with a nitrating reagent under conditions suitable for nitrating a free thiol group.

* * * * *

UNITED STATES PATENT AND TRADEMARK OFFICE
CERTIFICATE OF CORRECTION

PATENT NO. : 6,232,434 B1 Page 1 of 1
DATED : May 15, 2001
INVENTOR(S) : Jonathan S. Stamler, Eric J. Toone and Richard S. Stack It is certified that error appears in the above-identified patent and that said Letters Patent is hereby corrected as shown below:

<u>Title page,</u>
Item [73], after "Assignee:" delete "Duke University Medical Center" and insert therefor -- Duke University --;

<u>Column 24,</u>
Line 52, after the words "claim 24", delete "whrein" and insert therefor
-- wherein --; and
Line 57, after the words "SNO group per", delete "600amu" and insert therefor
-- 600 amu --.

Signed and Sealed this

Fourth Day of February, 2003

JAMES E. ROGAN
*Director of the United States Patent and Trademark Office*